United States Patent [19]

Shen et al.

[11] 4,402,979

[45] Sep. 6, 1983

[54] OPHTHALMIC FORMULATIONS OF 5-FLUORO-2-METHYL-1-(P-METHYLTHIOBENZYLIDENE)-3-INDENYLACETIC ACID

[75] Inventors: Tsung-Ying Shen, Westfield, N.J.; Philippe Conquet, Riom; Jean-Claude Le Douarec, Chamalieres, both of France

[73] Assignees: Merck & Co., Inc. & Laboratories, Rahway, N.J.; Merck, Sharp & Dohme-Chibret, Paris, France

[21] Appl. No.: 315,769

[22] Filed: Oct. 28, 1981

Related U.S. Application Data

[63] Continuation of Ser. No. 132,574, Mar. 21, 1980, abandoned.

[51] Int. Cl.$^3$ .............................................. A61K 31/19
[52] U.S. Cl. ................................................... 424/317
[58] Field of Search ......................................... 424/317

[56] References Cited

U.S. PATENT DOCUMENTS

| | | | |
|---|---|---|---|
| 3,609,184 | 9/1971 | Miyai et al. | 424/317 |
| 3,654,349 | 4/1972 | Shen et al. | 424/317 |
| 3,766,259 | 10/1973 | Sletzinger et al. | 424/317 |
| 3,888,902 | 6/1975 | Shen et al. | 424/317 |

OTHER PUBLICATIONS

Chem. Abst. 85, 87027(r) (1976)—Hucker et al.
Chem. Abst. 86, 183,227(x) (1977)—Duggan et al.
Chem. Abst. 91, 83,391(f) (1979)—Maki et al.
Chem. Abst. 91, 83,392(g) (1979)—Kurachi et al.
Intraocular Lens Symposium—Mar. 25-29 (1980) "Preliminary Report of Clinical Sucess of Topical Sulindac in Treatment of Clinical CME".

*Primary Examiner*—Douglas W. Robinson
*Attorney, Agent, or Firm*—William H. Nicholson; Edmunde D. Riedl; Mario A. Monaco

[57] ABSTRACT

This invention relates to ophthalmic preparations which include 5-fluoro-2-methyl-1-(p-methylthiobenzylidene)-3-indenylacetic acid or ophthalmologically acceptable salts thereof as the active entity for reducing or controlling inflammation of the eye.

9 Claims, No Drawings

OPHTHALMIC FORMULATIONS OF 5-FLUORO-2-METHYL-1-(P-METHYLTHIOBEN-ZYLIDENE)-3-INDENYLACETIC ACID

This is a continuation of application Ser. No. 132,574, filed Mar. 21, 1980, abandoned.

DISCLOSURE OF THE INVENTION

This invention relates to the suppression of inflammation in the eye. This invention further relates to the control of acute inflammation of the eye without the use of corticosteroids and immunosuppressive drugs. More particularly, this invention relates to the discovery that 5-fluoro-2-methyl-1-(p-methylthiobenzylidene)-3-indenylacetic acid and ophthalmically acceptable salts thereof are topically effective in the eye.

Inflammatory disease states of the eye, especially anterior uveitis and the post-operative intraocular inflammation associated with the intracapsular extraction of senile cataract are presently treated with steroidal anti-inflammatory drugs. For a variety of reasons in individual patients a steroidal preparation may be contraindicated. the present invention provides a means to effectively reduce or control inflammation of the eye without the use of steroidal preparations.

In practicing this invention, 5-fluoro-2-methyl-1-(p-methylthiobenzylidene)-3-indenylacetic acid or an ophthalmologically acceptable salt thereof such as the sodium or potassium is formulated into an ophthalmic preparation.

In such formulations, from 0.1% to 15% by weight can be employed. The objective is to administer a dose of from 0.1 to 10 mg. per eye per day to the patient, with treatment continuing so long as the inflammation persists.

Thus, in a solution, inert, ointment or suspension of the administered medicament from 0.1% to 15% 5-fluoro-2-methyl-1-(p-methylthiobenzylidene)-3-indenylacetic acid, or an equivalent percentage of a salt thereof is employed, the remainder being carrier, excipients, preservatives and the like.

In the form of a solution the 5-fluoro-2-methyl-1-(p-methylthiobenzylidene)-3-indenylacetic acid can be employed as the ophthalmologically acceptable salts such as the sodium and potassium salts obtained by neutralizing an equivalent of the acid with an equivalent of a suitable base such as, for example, the alkali metal hydroxide. When used in the form of a salt the active agent is added to an acceptable carrier which, for example, can be water or mixtures of water and water miscible solvents such as lower alkanols or aralkanols, and the like. The pharmaceutical preparation of the active entity may also contain non-toxic auxiliary substances such as emulsifying, preserving, wetting agents, bodying agents and the like, as for example, polyethylene glycols 200, 300, 400 and 600, carbowaxes 1,000, 1,500, 4,000, 6,000 and 10,000, bacterial components such as quaternary ammonium compounds, phenylmercuric salts known to have cold sterilizing properties and which are non-injurious in use, thimerosal, methyl and propyl paraben, benzyl alcohol, phenyl ethanol, buffering ingredients such as sodium chloride, sodium borate, sodium acetates, gluconate buffers, and other conventional ingredients such as sorbitan monolaurate, triethanolamine, oleate, polyoxyethylene sorbitan monopalmitylate, dioctyl sodium sulfosuccinate, monothioglycerol, thiosorbitol, ethylenediamine tetracetic acid, and the like. Additionally, suitable ophthalmic vehicles can be used as carrier media for the present purpose including conventional phosphate buffer vehicle systems, isotonic boric acid vehicles, isotonic sodium chloride vehicles, isotonic sodium borate vehicles and the like.

5-Fluoro-2-methyl-1-(p-methylthiobenzylidene)-3-indenylacetic acid as the acid is suitably administered in the form of ophthalmic pharmaceutical compositions adapted for topical administration to the eye such as a suspension, ointment, or as a solid inserts. Formulations of these compounds may contain from 0.01 to 15% and especially 0.5% to 2% of medicament. Higher dosages as, for example, about 10%, or lower dosages can be employed provided the dose is effective in reducing or controlling the inflammation. As a unit dosage from between 0.001 to 10.0 mg., preferably 0.005 to 2.0 mg., and especially 0.1 to 1.0 mg. of the compound is generally applied to the human eye, generally on a daily basis so long as the condition being treated exists.

These hereinbefore described dosage values are believed accurate for human patients and are based on the pharmacology of anti-inflammatory compounds, and the action of other entities in the human eye. They reflect the best mode known. As with all medications, dosage requirements are variable and must be individualized on the basis of the disease and the response of the patient. In rabbits the best mode is to employ a 5% to 10% weight suspension of 5-fluoro-2-methyl-1-(p-methylthiobenzyl-idene)-3-indenylacetic acid for reducing inflammation.

Ophthalmic suspensions for treating inflammation in the mamalian, human and animal, eye using 5-fluoro-2-methyl-1-(p-methylthiobenzylidene)-3-indenyl-acetic acid can be prepared by employing flocculating agents and deflocculating or suspending agents together, and by employing ratios of the various proportional amounts of medicament, vehicle, flocculating agent and deflocculating agent in the total suspension. Thus, the ophthalmic suspension can comprise from 1 to 15 mg./ml. of total suspension of the medicament, deflocculating agent as hereinafter defined, and flocculating agent as hereinafter defined, provided that the ratio of flocculating agent to deflocculating agent is from 7:1 to 30:1, especially 10:1 to 15:1, respectively, and the ratio of medicament to deflocculating agent is from 300:1 to 1:2, especially 60:1 to 1:1, respectively. In its preferred aspect, however, the opthalmic suspension composition of the present invention will contain from 1 to 15 mg./ml. and especially 2.5 to 10 mg./ml. of total suspension of medicament; 0.05 to 1.7 mg./ml. and especially 0.15 to 1.5 mg./ml. of total suspension of deflocculating agent; and 3 to 17 mg./ml. and especially 4 to 15 mg./ml. of total suspension of flocculating agent. The ophthalmic suspension compositions can also contain certain excipients whose presence is desirable in preparing an acceptable ophthalmic suspension. The nature and proportional amounts of these excipients will be discussed in detail hereinafter.

The flocculating agents employed are alkanols of 1 to 4 carbon atoms, and aromatic alcohols sepected from the group consisting of benzyl alcohol, $\beta$-phenyl-ethyl alcohol and cinnamyl alcohol, and mixtures of the above. Mixtures of varying proportions are suitable, and, for example, a mixture of benzyl alcohol and $\beta$-phenylethyl alcohol in a ratio of approximately 1:1 by weight has been found to give excellent results. As indicated previously, the flocculating agent will be employed in the ophthalmic suspension in amounts such that the ratio of flocculating agent to deflocculating agent is from 7:1 to 30:1, especially 10:1 to 15:1, respectively.

The deflocculating or suspending agents employed in the ophthalmic suspension compositions are products derived from the condensation of polymers of ethylene oxide containing from 10 to 50 oxyethylene repeating units, and esters of fat acids of 10 to 18 carbon atoms. Especially suitable are such condensation products from fat acid esters of sorbitol, particularly the lauric, stearic and oleic acid esters of sorbitol. The fatty acid esters may be employed as mixtures from naturally occurring oils, which are esters of fatty acids and glycerol. Thus, the deflocculating agent may be polyoxyethylene vegetable oil, available as Emulphor EL-719 from GAF Corporation. Naturally occurring fat acid mixtures may be employed to produce esters of sorbitol for condensation with polyoxyethylene. Thus, the deflocculating agent may be polyoxyethylene sorbitol lanolin, polyoxyethylene sorbitol tallow esters, and polyoxyethylene sorbitol tall oil, available respectively, as Atlas G-1441, Atlas G-3284, and Altox 1256 from Atlas Chemical Industries. Particularly preferred are esters of sorbitol and specific fat acids, especially lauric, stearic and oleic acids. Thus, the deflocculating agent may be polyoxyethylene sorbitan monolaurate, polyoxyethylene sorbitan monostearate, or polyoxyethylene sorbitan monoleate, available, respectively, as Atlas G-7596J, Tween 80 from Atlas Chemical Industries. The last named product, Tween 80, which contains 20 oxyethylene units, has been found to be especially suitable. As indicated previously, the deflocculating agent will be employed in the ophthalmic suspension in amounts such that the ratio of medicament to deflocculating agent is from 300:1 to 1:2, especially 60:1 to 1:1, respectively.

By use of the particular flocculating and deflocculating agents described above, and in the critical range of proportionate amount ratios of the present invention, it is possible to obtain acceptable ophthalmic suspension compositions for 5-fluoro-2-methyl-1-(p-methylthiobenzylidene)-3-indenylacetic acid which have the highly desirable properties of having the suspended material uniformly dispersed therein during the period of administration to the eye of the patient, while at the same time facilitating easy redispersion of that material after its flocculation and separation in the ophthalmic suspension composition.

In addition to the medicament, flocculating and deflocculating agents and water, conventional excipients and other materials are advantageously employed in preparing the ophthalmic suspension compositions of the present invention in accordance with good pharmaceutical practice. For example, the ophthalmic suspensions are sterile and preferably contain a bacteriological preservative to maintain sterility during use. Quarternary ammonium bacteriostats such as benzalkonium chloride may be used as well as phenyl mercuric acetate, phenyl mercuric nitrate, trimerosal, benzyl alcohol, or β-phenylethyl alcohol. These bacteriostats may suitably be used in a range of from 0.01 to 3.0 mg./ml. and preferably 0.1 to 0.2 mg./ml. of total suspension. As antioxidant may also be used to prevent oxidation of the medicament. Suitable antioxidants include sodium bisulfate, N-acetyl cysteine salts, sodium ascorbate, sodium meta bisulfite, sodium acetone bisulfite and other acceptable anti-oxidants known to the pharmaceutical art. These antioxidants may suitably be used in a range of 0.1 to 10.0 mg./ml. and preferably 0.2 to 3.5 mg./ml. In conjunction with the antioxidants, chelating agents such as disodium edetate may also be employed.

Viscosity inducing agents helpful in suspension characteristics of the composition, including cellulose derivatives such as hydroxymethyl cellulose, hydroxypropyl cellulose and methyl cellulose, may also be used in the formulation. For this purpose, one may use from 5.0 to 10.0 mg./ml. and preferably from 1.5 to 3.5 mg./ml. of such agents. Lecithin may also be used to produce helpful suspension characteristics for the ophthalmic suspension composition, being employed for this purpose in amounts of from 0.05 to 1.0 mg./ml. of total suspension, and preferably from 0.1 to 0.4 mg./ml. A humectant is also sometimes used to help retain the water of the formulation in the eye. High molecular weight sugars are suitably used for this purpose such as sorbitol and dextrose in a concentration of from 0.1 to 10.0 mg./ml. and especially 0.5 to 2.0 mg./ml. Finally, since the formulation is autoclaved to obtain initial sterility an autoclaving aid such as sodium chloride is normally added to the formulation. The ophthalmic suspension compositions of the present invention are prepared by methods well known in the pharmaceutical art. For example, (1) there is first prepared a supersaturated NaCl aqueous solution such that the volume of water does not exceed $2\frac{1}{2}$ times the amount of NaCl, and excess NaCl remains undissolved. (2) The medicament is then dispersed in the saline solution of (1) until a wet paste is formed. (3) The paste is sterilized by autoclaving at 121° C. under 15 psig. pressure. (4) The viscosity inducing agent which is employed is then dispersed in water, clarified, and sterilized by autoclaving. (5) The other components of the total suspension composition are then added to water to form a solution. (6) The medicament paste from step (3) is then added aseptically to the viscosity inducing agent dispersion of step (4), and mixed. (7) The remaining suspension ingredients, prepared in step (5), are added aspectically to the mixture from step (6) by way of sterilizing membrane. (8) Sufficient water is added to the suspension from step (7) to give the total desired volume. (9) The suspension is then aseptically homogenized at 1500–2200 psig., subdivided and distributed to suitable sterile containers.

The following examples illustrate preparation of the improved ophthalmic suspension compositions of the present invention.

EXAMPLES 1-4

The following materials are admixed in a 1250 ml. bottle: 20.6 g. of 5-fluoro-2-methyl-1-(p-methylthiobenzylidene)-3-indenylacetic acid which is a sufficient amount of medicament to result in a concentration of 10 mg. per ml. in the final samples, allowing for previously established 3.0% average; 0.4 g. sodium bisulfite, 12 g. NaCl, and 28 ml. water (at 180° F.) The mixture (I) is autoclaved for 30 minutes at 121° C. under 15 psig. Separately, 3 g. of hydroxyethylcellulose in 720 ml. of water (II) and 0.4 g. of lecithin in 80 ml. of water (III) were autoclaved for 30 minutes at 121° C. Then, III is admixed with I for 2 hours, and the resulant mixture poured into II. Another mixture (IV) is prepared from 20 g. of sorbitol, 2.36 ml. of benzalkonium chloride, 10 g. of disodium edetate, and water to give a final solution volume of 900 ml. Then, IV is added to the mixture of I, II, and III in sufficient quantity to give 1.8 l. overall. The 1.8l mixture of I, II, III, and IV is then taken and homogenized using a homogenizer at 2000 psig. Stock solutions are then prepared for polyoxyethylene (20) sorbitan monooleate by dissolving 3 g. of the material in 100 ml. of water, and of benzyl alcohol/β-phenylethyl alcohol by admixing 50 ml. of each alcohol. Varying quantities of the two stock solutions are then added to four 90 ml. aliquots of the homogenized mixture of I, II, III, and IV prepared as described above, together with sufficient water to give a total of 100 ml. for each of four different samples.

EXAMPLE 5

| Solution Composition | a |
|---|---|
| 5-fluoro-2-methyl-1-(p-methylthiobenzylidene)-3-indenylacetic acid | 0.1 mg. |
| Peanut oil q.s. ad. | 0.10 mg. |

The solution is rendered sterile by filtration through a sterilizing filter.

EXAMPLE 6

| | |
|---|---|
| 5-fluoro-2-methyl-1-(p-methylthiobenzylidene)-3-indenylacetic acid | 0.5 mg. |
| Petrolatum q.s. ad. | 1 gram |
| and the petrolatum are aseptically combined. | |

EXAMPLE 7

| | |
|---|---|
| 5-fluoro-2-methyl-1-(p-methylthiobenzylidene)-3-indenylacetic acid | 0.1 mg. |
| Hydroxypropylmethyl cellulose q.s. | 12 mg. |

Ophthalmic inserts are manufactured from a solvent cast film prepared by making a viscous solution of the powder blend using a methanol/water solvent system (10 ml. methanol is added to 2.5 g. of powder blend, to which 11 ml. of water (in three divided portions) is added). The solution is placed on a Teflon (polytetrafluoroethylene) plate and allowed to dry at ambient conditions. After drying, the film is placed in an 88% relative humidity cabinet until it is pliable. Appropriately sized inserts are then cut from the film.

EXAMPLE 8

| | |
|---|---|
| 5-fluoro-2-methyl-1-(p-methylthiobenzylidene)-3-indenylacetic acid | 0.1 mg. |
| Hydroxypropyl Cellulose q.s. a.d. | 12 mg. |

Ophthalmic inserts are manufactured from compression molded films which are prepared on a Carver Press by subjecting the powder mixture of the above ingredients to a compressional force of 12,000 lbs. (gauge) at 350° F. for one minute. The film is cooled under pressure by having cold water circulate in the platen. Ophthalmic inserts are then individually cut from the film with a punch. Each insert is placed into a vial, which is then placed in a humidity cabinet (88% relative humidity at 30° C.) for two to four days. After removal from the humidity cabinet, the vials are stoppered and then capped. The vials containing the hydrated insert are then sterilized by means known in the art such as irradiation with high energy electron beams, gamma radiation with a suitable radiation source such as $Co^{60}$.

The pharmaceutical preparation may also be in the form of a solid insert. For example, one may use a solid water soluble polymer as the carrier for the medicament. Inserts that are known in the art that are suitable for use with this include those set forth and described in U.S. Pat. Nos. 3,993,071; 3,986,510; 3,868,445; and 3,867,510 employing the formulation and fabrication techniques described therein. The polymer used to form the insert may be any water soluble non-toxic polymer, for example, cellulose derivatives such as methyl cellulose, alkali metal carboxymethyl cellulose, hydroxyethyl cellulose, hydroxypropyl cellulose, hydroxypropylmethyl cellulose, acrylates such as polyacrylic acid salts, ethylacrylates; polyacrylamides; natural products such as collagen gelatin, alginates, pectins, tragacanth, karaya, chondrus, agar, acacia; the starch derivatives such as starch acetate, hydroxyethyl starch ethers, hydroxypropyl starch, as well as other synthetic derivatives such as polyvinyl alcohol, polyvinyl pyrrolidone, polyvinyl methyl ether, polyethylene oxide, neutralized carbopol and xanthan gum and mixtures of said polymer.

If a solid insert is employed, it preferably is prepared from cellulose derivatives such as methyl cellulose, hydroxyethyl cellulose, hydroxypropyl cellulose or hydroxypropylmethyl cellulose or from other synthetic materials such as polyvinyl alcohol, polyvinyl pyrrolidone, polyethylene oxide or polyvinyl methylether.

Hydroxypropyl cellulose, one of the preferred polymers for the preparation of the insert is available in several polymeric forms, all of which are suitable in the preparation of these inserts. Thus, the product sold by Hercules, Inc. of Wilmington, Del., under the name KLUCEL such as KLUCEL HF, HWF, MF, GF, JF, LF and EF, which are intended for food or pharmaceutical use, are particularly useful. The molecular weight of these polymers useful for the purposes described herein may be at least 30,000 to about 1,000,000 or more.

Similarly, an ethylene oxide polymer having a molecular weight of up to 5,000,000 or greater, and preferably 100,000 to 5,000,000 can be employed.

Further, for example, POLYOX, a polymer supplied by Union Carbide Co., may be used having a molecular weight of about 50,000 to 5,000,000 or more and preferably 3,000,000 to 4,000,000. Other specific polymers which are useful are polyvinyl pyrrolidine having a molecular weight of from about 10,000 to about 1,000,000 or more, preferably up to about 350,000 and especially about 20,000 to 60,000; polyvinyl alcohol having a molecular weight of from about 30,000 to 1,000,000 or more, particularly about 400,000 and especially from about 100,000 to about 200,000; hydroxypropylmethyl cellulose having a molecular weight of from about 10,000 to 1,000,000 or more, particularly up to about 200,000 and especially about 80,000 to about 125,000; methyl cellulose having a molecular weight of from about 10,000 to about 1,000,000 or more, preferably up to about 200,000 and especially about 50 to 100,000; and CARBOPOL (carboxyvinyl polymer) of B. F. Goodrich and Co. designated as grades 934, 940 and 941.

For the purpose of this invention the type and molecular weight of the polymer is not critical. Any water soluble polymers can be used which have an average molecular weight which will afford dissolution of the polymer and, accordingly, the medicament in any desired length of time. The inserts, therefore, can be prepared to allow for retention and, accordingly, effectiveness in the eye for any desired period. The insert can be in the form of a square, rectangle, oval, circle, doughnut, semi-circle, ¼ moon shape, and the like. Preferably, the insert is in the form of a rod, doughnut, oval or ¼ moon. The insert can be readily prepared, for example, by dissolving the medicament and the polymer in a suitable solvent and evaporating the resulting solution to afford a thin film of the polymer which can then be subdivided to prepare inserts of appropriate size. Alternatively, the insert can be prepared by intimately admixing polymer and the medicament and thereafter molding the resulting mixture under the influence of heat and pressure to form a thin film. Preferably, the inserts are prepared by molding or extrusion procedures well known in the art. The molded or extruded product can then be subdivided to afford inserts of suitable size for administration in the eye.

The insert can be of any suitable size which readily fits into the eye. For example, castings or compression molded films having a thickness of about 0.25 mm. to 1.50 mm. can be subdivided to obtain suitable inserts. Rectangular segments of the cast or compressed film having a thickness between about 0.5 and 1.5 mm. can be cut to afford shapes such as rectangular plates of 4×5-20 mm. or ovals of comparable size. Similarly, extruded rods having a diameter between about 0.5 and 1.5 mm. can be cut into suitable sections to provide the desired amount of polymer. For example, rods of 1.0 to 1.5 mm. in diameter and about 2-20 mm. long are found to be satisfactory. The inserts may also be directly formed by injection molding. It is preferred that the ophthalmic inserts containing the medicament of the present invention be formed so that they are smooth and do not have any sharp edges or corners which could cause damage to the eye. Since the term smooth and sharp edges or corners are subjective terms, in this application these terms are used to indicate that excessive irritation of the eye will not result from the use of the insert.

The medicated ocular inserts can also contain plasticizers, buffering agents, appropriate inert fillers, and preservatives. Plasticizers suitable for this purpose must, of course, also be completely soluble in the lacrimal fluids of the eye. Examples of suitable plasticizers that might be mentioned are water, polyethylene glycol, propylene glycol, glycerine, trimethylol propane, di- and tripropylene glycol, hydroxypropyl sucrose and the like. Typically, such plasticizers can be present in the medicated ophthalmic insert in an amount ranging from up to 1 to about 30% by weight. A particularly preferred plasticizer is water which is present in amounts of at least about 5% up to about 40%. In actual practice, a water content of from about 10% to about 20% is preferred since it may be easily accomplished and adds the desired softness and pliability to the insert.

When plasticizing the solid medicinal product with water, the product is contacted with air having a relative humidity of at least 40% until said product picks up at least about 5% water and becomes softer and more pliable. In a preferred embodiment, the relative humidity of the air is from about 60% to about 99% and the contact is continued until the water is present in the product in amounts of from about 10% to about 20%.

Suitable water soluble preservatives which may be employed in the insert are alkali bisulfate, alkali thiosulfate, ascorbate, benzalkonium chloride, chlorobutanol, thimerosal, phenylmercuric acetate, phenylmercuric borate, parabens, benzyl alcohol and phenyl ethanol. These agents may be present in amounts of from 0.001 to 5% by weight of solid insert, and preferably 0.1 to 2%.

Suitable water soluble buffering agents are alkali, alkali earth carbonates, phosphates, bicarbonates, citrates, borates, and the like, such as sodium or potassium phosphate, citrate, borate, acetate, bicarbonates and carbonate. These agents may be present in amounts sufficient to obtain a pH of the system of between 5.5 to 8.1 and especially 7-8; usually up to about 2% by weight of polymer. The insert may contain from about 1 mg. to 100 mg. of water soluble polymer, more particularly from 5 to 50 mg. and especially from 5 to 20 mg. The medicament is present from about 0.1 to about 25% by weight of insert.

It is highly preferred that the solid inserts of this invention are available for use by the patient in a pathogen free condition. Thus, it is preferred to sterilize the inserts and so as insure against recontamination, the sterilization is preferably conducted after packaging. The best mode of sterilizing is to employ ionizing irradiation including irradiation emanating from Cobalt 60 or high energy electron beams.

After packaging a convenient quantity of inserts, usually a single dose, the package is exposed to a sterilizing quantity of radiation. The preferred packaging employs sealing the inserts between layers of film or foil and then sealing or laminating the layers together about the edges. The techniques for performing the sterilization are well known and accepted, for example, as outlined in International Atomic Energy Commission *Code of Practice for Radiosterilization of Medical Products,* 1967, pp. 423-431; and Block, *Disinfection, Sterilization and Preservation,* 2nd Ed., Lea & Febiger, Philadelphia, 1977, pp 542-561.

The required quantity of irradiation can be determined experimentally by testing irradiated inserts for viable bacteria. Generally, the amount of irradiation desired to achieve sterilization is defined by the $D_{10}$ value. The $D_{10}$ value is the radiation dose that will reduce a given population of organisms by a factor of 10. Base on $D_{10}$ values, experimentally obtained for *Bacillus pumilus,* and presterilization contamination levels, a dose of 1.36 megarads is effective in obtaining a sterile product.

What is claimed is:

1. An ophthalmic composition for reducing ocular inflammation comprising from 0.1 to 15% by weight of 5-fluoro-2-methyl-1-(p-methylthiobenzylidene)-3-indenylacetic acid or an ophthalmologically acceptable salt thereof together with an ophthamologically acceptable carrier for topical application to an affected eye.

2. The composition according to claim 1 wherein there is included in the composition a bacteriostat.

3. The composition according to claim 2 wherein the ophthalmic composition is a suspension comprising flocculating and deflocculating agents wherein the ratio of flocculating agent to deflocculating agent is from 7:1 to about 30:1.

4. The composition according to claim 2 wherein the ophthalmic composition is an insert.

5. The composition according to claim 4 wherein the insert is soluble in lacrimal fluids.

6. A method of treating ocular inflammation comprising applying to the eye an ophthalmic composition comprising an inflammation reducing amount of 5-fluoro-2-methyl-1-(p-methylthiobenzylidene)-3-indenylacetic acid or an ophthalmologically acceptable salt thereof.

7. The method according to claim 6 wherein the ophthalmic composition is a suspension comprising flocculating and deflocculating agents wherein the ratio of flocculating agent to deflocculating agent is from 7:1 to about 30:1.

8. The method according to claim 6 wherein the opthalmic composition is in the form of an insert.

9. The method according to claim 8 wherein the insert is soluble in lacrimal fluids.

* * * * *